United States Patent
Freyssinet et al.

(12)

(10) Patent No.: US 6,235,530 B1
(45) Date of Patent: *May 22, 2001

(54) **PRODUCTION OF PLANTS RESISTANT TO ATTACKS BY *SCLEROTINIA SCLEROTIORUM* BY THE INTRODUCTION OF A GENE ENCODING AN OXALATE OXIDASE**

(75) Inventors: Georges Freyssinet, St Cyr au Mont d'Or; Alain Sailland, Lyons, both of (FR)

(73) Assignee: Rhone-Poulenc Agrochimie (FR)

(*) Notice: Subject to any disclaimer, the term of this patent is extended or adjusted under 35 U.S.C. 154(b) by 0 days.

This patent is subject to a terminal disclaimer.

(21) Appl. No.: 08/447,703

(22) Filed: May 23, 1995

Related U.S. Application Data

(62) Continuation of application No. 08/400,006, filed on Mar. 6, 1995, which is a continuation of application No. 08/207,105, filed on Mar. 8, 1994, now abandoned, which is a continuation of application No. 07/941,135, filed as application No. PCT/FR92/00195 on Mar. 4, 1992, now abandoned.

(30) Foreign Application Priority Data

Mar. 5, 1991 (FR) .................................................. 91 02874

(51) Int. Cl.$^7$ .............................. A01H 5/00; C12N 5/04; C12N 15/29; C12N 15/82
(52) U.S. Cl. .................. 435/468; 435/69.2; 435/469; 435/419; 435/69.8; 800/301; 800/306; 800/278
(58) Field of Search .................... 435/69.2, 172.3, 435/240.4, 320.1, 468, 469, 69.8; 800/200, 205, 250, DIG. 15, 278, 279, 298, 306, 301; 935/22; 47/58, 58.07

(56) References Cited

U.S. PATENT DOCUMENTS 5,866,778 * 2/1999 Hartman et al. ..................... 800/205

OTHER PUBLICATIONS

Dratewka–Kos et al., "Polypeptide Structure of Germin as Deduced from cDNA Sequencing," *The Journal of Biological Chemistry* (1989) 264(9):4896–4900.

Lane et al., "Homologies between Members of the Germain Gene Family in Hexaploid Wheat and Similarities between These Wheat Germins and Certain Physarum Spherulins," *The Journal of Biological Chemistry* (1991) 266(16):10461–10469.

* cited by examiner

*Primary Examiner*—David T. Fox
*Assistant Examiner*—Melissa L. Kimball
(74) *Attorney, Agent, or Firm*—Burns, Doane, Swecker & Mathis, L.L.P.

(57) ABSTRACT

The present invention provides a DNA sequence encoding an oxalate oxidase. The oxalate oxidase may be used for the resistance of plants to diseases caused by Sclerotinia sp. It may be provided by a chimeric gene and a vector containing the coding sequence. It may be used to confer on plants an increased resistance to diseases caused by Sclerotinia sp.

20 Claims, 2 Drawing Sheets

DNA OF OXALIC OXIDASE
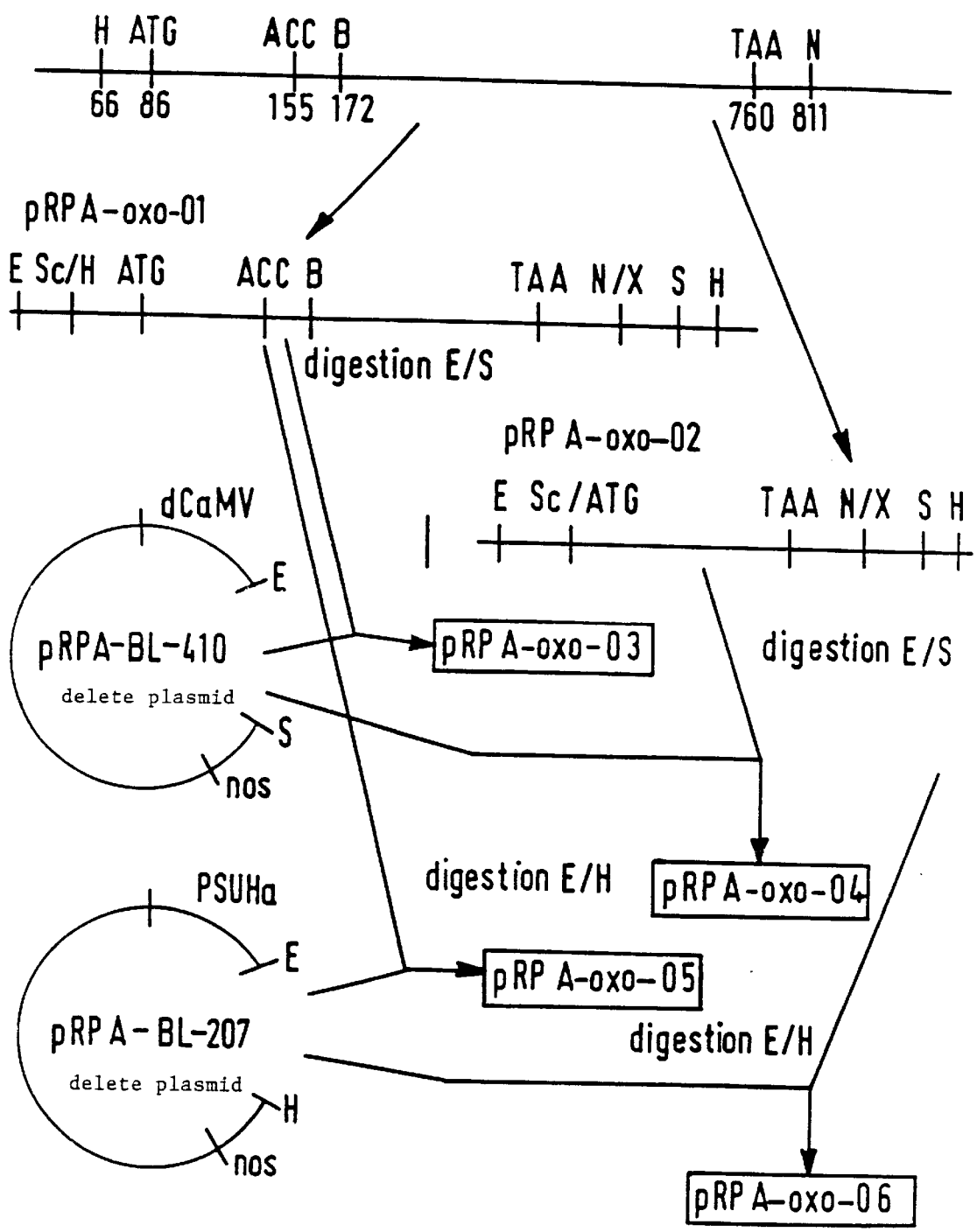

FIG. 2

_____5'-Untranslated Sequence: 85_____
1-gcagcagcaacaaccagtgccatagacactctccatcaacaaactctagctgatcaatcctagctaagcttattacatagcaagc _____Signal-Peptide Coding Sequence: 69_____
```
 86- ATG GGG TAC TCC AAA ACC CTA GTA GCT GGC CTG TTC GCA ATG
   1 M   G   Y   S   K   T   L   V   A   G   L   F   A   M
128- CTG TTA CTA GCT CCG GCC GTC TTG GCC
  15 L   L   L   A   P   A   V   L   A
```

_____Mature-Protein Coding Sequence: 603_____
```
155- ACC GAC CCA GAC CCT CTC CAG GAC TTC TGT GTC GCC GAC CTC
   1 T   D   P   D   P   L   Q   D   F   C   V   A   D   L
197- GAC GGC AAG GCG GTC TCG GTG AAC GGG CAC ACG TGC AAG CCC
  15 D   G   K   A   V   S   V   N   G   H   T   C   K   P
239- ATG TCG GAG GCC GGC GAC GAC TTC CTC TTC TCG TCC AAG TTG
  29 M   S   E   A   G   D   D   F   L   F   S   S   K   L
281- GCC AAG GCC GGC AAC ACG TCC ACC CCG AAC GGC TCC GCC GTG
  43 A   K   A   G   N   T   S   T   P   N   G   S   A   V
323- ACG GAG CTC GAC GTG GCC GAG TGG CCC GGT ACC AAC ACG CTG
  57 T   E   L   D   V   A   E   W   P   G   T   N   T   L
365- GGT GTG TCC ATG AAC CGC GTG GAC TTT GCT CCC GGA GGC ACC
  71 G   V   S   M   N   R   V   D   F   A   P   G   G   T
407- AAC CCA CCA CAC ATC CAC CCG CGT GCC ACC GAG ATC GGC ATC
  85 N   P   P   H   I   H   P   R   A   T   E   I   G   I
449- GTG ATG AAA GGT GAG CTT CTC GTG GGA ATC CTT GGC AGC CTC
  99 V   M   K   G   E   L   L   V   G   I   L   G   S   L
491- GAC TCC GGG AAC AAG CTC TAC TCG AGG GTG GTG CGC GCC GGA
 113 D   S   G   N   K   L   Y   S   R   V   V   R   A   G
533- GAG ACG TTC CTC ATC CCA CGG GGC CTC ATG CAC TTC CAG TTC
 127 E   T   F   L   I   P   R   G   L   M   H   F   Q   F
575- AAC GTC GGT AAG ACC GAG GCC TCC ATG GTC GTC TCC TTC AAC
 141 N   V   G   K   T   E   A   S   M   V   V   S   F   N
617- AGC CAG AAC CCC GGC ATT GTC TTC GTG CCC CTC ACG CTC TTC
 155 S   Q   N   P   G   I   V   F   V   P   L   T   L   F
659- GGC TCC AAC CCG CCC ATC CCA ACG CCG GTG CTC ACC AAG GCA
 169 G   S   N   P   P   I   P   T   P   V   L   T   K   A
701- CTC CGG GTG GAG GCC AGG GTC GTG GAA CTT CTC AAG TCC AAG
 183 L   R   V   E   A   R   V   V   E   L   L   K   S   K
743- TTT GCC GCT GGG TTT
 197 F   A   A   G   F
```

_____3'-Untranslated Sequence: 318_____
758-taatttctaggagccttccctgaaatgataattatataattccatatatgcatgctagcaaaatttaataattctcaccagaagacatgt
attcaagtttcaggttaatctcgcatgtagtcgtgtaataagattgaacaagttagcctcatggtgtagccttcgatcagaaccaatatga
ggaattgaatgtactacttttattgtcgtctttgttcttttcactgaacggaatatataataagcattttcgta₆₃

PRODUCTION OF PLANTS RESISTANT TO ATTACKS BY *SCLEROTINIA SCLEROTIORUM* BY THE INTRODUCTION OF A GENE ENCODING AN OXALATE OXIDASE

This application is a continuation of application Ser. No. 08/400,006, filed Mar. 6, 1995, which is a continuation of application Ser. No. 08/207,105, filed Mar. 8, 1994, now abandoned, which is a continuation of application Ser. No. 07/941,135, filed Dec. 3, 1992, now abandoned, which is a 371 of PCT/FR92/00195, filed Mar. 4, 1992.

BACKGROUND OF THE INVENTION

1. Field of the Invention

The subject of the present invention is a gene encoding an oxalate oxidase, the protein encoded by this gene, the chimeric genes comprising this gene and their use for transformation of dicotyledonous plants in order to confer on those plants a resistance to fungal diseases.

2. Description of the Related Art

Sclerotiniosis is a major fungal disease which affects a large number of dicotyledons. The causative agent, *Sclerotinia sclerotiorum* is a polyphagous fungus which exhibits little host specificity.

The fungus can attack the plant either directly at the level of the stem, or at the level of the leaves and then spread to the stem, or at the level of the floral capitulum. In the first two cases, the plant withers from disruption to food supply. In the last case, the flower withers, damaging the harvest.

The fungus produces lytic enzymes which degrade the cell wall of the infected plant and promote its development in the plant. These enzymes play an important role in pathogenicity, but do not appear to be sufficient. This fungus also produces oxalic acid (Godoy et al. (1990). *Physiol. Molec. Plant. Pathol).* 37:179–181. This oxalic acid causes a decrease in pH in the infected tissues, promoting hydrolysis of the cell wall by the lytic enzymes. A reduction in the production of oxalic acid or degradation of this oxalic acid should permit a slowing-down or even an inhibition of the development of the fungus.

In order to develop a Sclerotinia resistant plant, the strategy of detoxification of oxalic acid may be used. The degradation of this acid will limit the decrease in intracellular pH of the plant tissue attacked, the lytic enzymes will thereby be functioning at a value too far-removed from their optimum pH to be really active and efficient. This will lead to a decrease in the pathogenicity of the fungus.

Oxalate oxidase which catalyses the following reaction:

$$C_2O_4H_2 \xrightarrow[\text{oxalate oxidase}]{O_2} 2CO_2 + H_2O_2$$

may be used to achieve this objective.

Oxalate oxidase is isolated from various plants, generally from monocotyledons (Pieta et al. (1982) *Preparative Biochemistry* 12(4):341–353): the protein may for example be purified from barley using conventional chromatographic techniques (Sephadex G-75 filtration gels and MonoQ ion exchange gels, Pharmacia), by monitoring the enzymatic activity according to the following calorimetric procedure (Obzansky and Richardson (1983) *Clin. Chem.* 29(10):1815–1819):

$$\text{Oxalic acid} + O_2 \xrightarrow[\text{oxalate oxidase}]{} 2CO_2 + H_2O_2 +$$

$$H_2O_2 + \text{MBTH} + \text{DMA} \xrightarrow[\text{peroxidase}]{} \text{indamine} + H_2O +$$

MBTH = 3-methyl-2-benzothiazolinone hydrazone
DMA = N,N-dimethylalinine

This has made it possible to purify a protein which, on acrylamide gel under denaturing conditions, has a molecular mass of 26,000 daltons. Part of the purified oxalate oxidase was used to obtain rabbit anti-oxalate oxidase antibodies; the remainder of the protein was used to carry out the sequencing of the native protein (N-terminal) or, after cyanogen bromide cleavage, the sequencing of certain internal peptides. The results obtained are as follows (SEQ ID NOS:1–2):

N-terminal: SIDPDPLQDF-VADLDGKAVSVNGH

Internal peptide No. 2: HFQFNVGKTEAY cDNA

Comparison of the peptide sequences described above with the data contained in the protein library Swiss-Prot enabled us to identify a wheat protein called Germine and published in 1989 by Dratewka-kos et al. Experiments were carried out and they enabled us to determine that the cDNA published by the authors encodes a protein of 201 amino acids which exhibits an oxalate oxidase activity. For the rest of the description of the experiments presented in this patent, we will use the nucleotide numbering in FIG. 2 in the article by the authors published in J. Biol. Chem., 264, 4896–4900. This sequence is reproduced as FIG. 2 of the present application.

The sequence of this cDNA is 1075 nucleotides in length with an untranslated 5' of 85 residues, an open reading frame of 672 nucleotides (from position 86 to 757) and an untranslated 3' of 318 residues.

Comparison of the protein sequence deduced from the cDNA sequence with that obtained by sequencing the native protein shows that the cDNA encodes not only mature oxalate oxidase but also a signal peptide of 23 amino acids in the N-terminal part. Oxalate oxidase is therefore synthesised in the form of a preprotein (signal peptide plus mature peptide) which undergoes maturation by removal of the signal peptide in order to release the mature active enzyme.

BRIEF DESCRIPTION OF THE DRAWINGS

FIG. 1 schematically illustrates the construction of plasmid pRPA-oxo-2.

FIG. 2 illustrates the DNA and amino acid sequence encoding the 201 amino acid oxalate oxidase of the present invention.

In the following, we will use either the part encoding the preprotein (nucleotides 86 to 757), or only that part encoding the mature protein (from position 155 to 757). In the latter case, an AUG codon (encoding a methionine) should be placed before the ACC codon (encoding threonine, the first amino acid of the mature protein).

The attacks on plants by *Sclerotinia sclerotiorum* being essentially through the stem or the plant, it is advantageous to be able to express oxalate oxidase either in chlorophyllous tissues, and for that the promoter of the small subunit of ribulose 1,5-di-phosphate carboxylase of *Helianthus annuus* (SSUHa, Waksman et al., 1987) *Nucl. Acid Res.* 15:7181) may be used, or in the various tissues of the plant, and for that we will use the ubiquitous promoter of the 35S RNA of the cauliflower mosaic virus (CaMV 35S) part of which was duplicated and which is called "double CaMV".

SUMMARY OF THE INVENTION

The chimeric genes according to the invention may be for example constructed from the following elements:

A. Double CaMV promoter followed by that part of the oxalate oxidase cDNA encoding the pre-protein (signal peptide plus mature peptide) and the terminator "nos" obtained from the pTi 37 nopaline synthase gene (Bevan et al., A chimeric antiobiotic resistance gene as a selectable marker for plant cell transformation. *Nature* 304(5922): 184–187, 1983).

B. Double CaMV promoter followed by that part of the oxalate oxidase cDNA encoding only the mature protein followed by the terminator "nos".

C. Gene identical to "A" but with the promoter of the small subunit of sunflower ribulose 1,5-diphosphate carboxylase (SSUHa) in place of the double CaMV.

D. Gene identical to "B" but with the promoter of the SSUHa in place of the double CaMV.

Each chimeric gene is introduced into the plant cell by a system using Agrobacterium or any other system otherwise known for transforming plant cells. Plants are regenerated from these transformed cells. They exhibit an increased tolerance to *Sclerotinia sclerotiorum*.

DETAILED DESCRIPTION OF THE INVENTION

EXAMPLE 1

Preparation of Two Coding Sequences

Preprotein: it is obtained from the cDNA described above, digested with HindIII (in position 66). The cohesive end obtained is made blunt by treating with Klenow polymerase. This DNA is then digested with NheI (in position 811).

The plasmid pUC 19 (Yanisch-Perron et al., 1985) is digested in parallel with SacI.

The cohesive end obtained is made blunt by treating with Klenow polymerase. The plasmid is then digested with XbaI (compatible with NheI).

The cDNA fragment and plasmid prepared above are ligated. The new plasmid thus obtained is called pRPA-oxo-01 and its map is presented in FIG. 1.

B. Mature protein: it is obtained from the cDNA described above after digestion with BstNI (in position 173). The fragment obtained and the linker of the sequence (SEQ ID NO:3):

5' 3' ATGACCGACCCAGACCCTCTCC TACTG-GCTGGGTCTGGGAGAGGT 3' 5' are ligated. This leads to a modification of the N-terminal sequence (SEQ ID NOS:4–5) of the mature protein which passes from TDPDPLQ to MTDPDPLQ.

This cDNA fragment is then digested with NheI (in position 811) so that it can then be ligated with the plasmid pUC19 prepared as described in the paragraph above. The new plasmid thus formed is called pRPA-oxo-02 and its map is presented in FIG. 1.

EXAMPLE 2

Preparation of the Chimeric Genes:

a. Preparation of the vectors containing the promoter and the terminator nos;

example double CaMV: this vector is obtained from the plasmid pRPA-BL-410 obtained in the following manner:

"Transit Peotide of the SSU of Maize RuBisCO/AroA Gene" Fusion:

The transit peptide of the SSU of the maize RuBisCO gene is derived from an EcoRI-SphI fragment of 192-bp; it is obtained from the cDNA corresponding to the SSU gene of the maize RuBisCO gene described by Lebrun et al. (1987) *Nucl. Acid Res.* 15:4360 with an NcoI site spanning the initiation codon for translation and an SphI site corresponding to the cleavage site of the transit peptide.

The translational fusion between the maize transit peptide and the bacterial EPSPS gene is obtained by treating the SphI end with the bacteriophage T4 polymerase and by ligating it with the Klenow polymerase-treated NcoI end of the AroA gene of pRPA-BL 104 recut with EcoRI.

Transit Peptide of the SSU of maize RuBisCO/Sequence of 22 Amino Acids of the Mature Part of the SSU of Maize RuBisCO/AroA Gene Fusion In a similar fashion, an EcoRI-HindII fragment of 228 bp of the cDNA of the SSU of maize RuBisCO gene is ligated with the Klenow polymerase-treated NcoI end of the AroA gene of pRPA-BL 104 and recut with EcoRI. A translational fusion is obtained between the transit peptide of the SSU of maize RuBisCO, the 22 amino acids of the mature part of the SSU of maize RuBisCO and the bacterial EPSPS gene.

Transit Peotide of the SSU of Sunflower RuBisCO

The fragment is obtained from the cDNA isolated by Waksman and Freyssinet (1987) (*Nucl. Acid Res.* 15:1328). A SphI site was created according to the method of Zoller and Smith (1984) (*Methods Enzymol.* 154:329) at the cleavage site of the transit peptide. The transit peptide of the SSU of sunflower RuBisCO thus obtained is an EcoRI-SphI fragment of 171 bp.

Transit Peptide of the SSU of Sunflower RuBisCO/Sequence of 22 Amino Acids of the Mature Part of the SSU of Maize RuBisCO/AroA Gene Fusion The construct containing the transit peptide of the SSU of maize RuBisCo/sequence of 22 amino acids of the SSU of maize RuBisCO of the mature part of the maize gene fusion was cut with EcoRI-SphI of 171 bp corresponding to the transit peptide of the SSU of the said sunflower RuBisCO gene. The resulting construct exhibits a substitution of the EcoRI-SphI fragments and is a translational fusion, "transit peptide of the SSU or sunflower RuBisCO/sequence of 22 amino acids of the mature part of the SSU of maize RuBisCO/AroA gene.

The EcoRI-SalI fragment was ligated with the SalI-SstI fragment containing the 3' nos sequence and the right end of the T-DNA. The resulting EcoRI-SstI fragment comprising "transit peptide of the SSU of sunflower RuBisCO/sequence 22 of amino acids of the mature part of the SSU of maize RuBisCO/AroA gene/3' nos/T-DNA right end" is substituted for the EcoRI-SstI fragment containing the right end of the T-DNA of the plasmid 150 A alpha 2 containing the double CaMV promoter. The transcriptional fusion "double CaMV/transit peptide of the SSU of sunflower RuBisCO/sequence of 22 amino acids of the mature part of the SSU of maize RuBisCO/AroA gene/3' nos" in the vector 150 A alpha 2 was called pRPA-BL 294.

"Transit Peptide of the SSU of Sunflower RuBisCO/Sequence of 22 Amino Acids of the SSU of Maize RuBisCO/Transit Peptide of the SSU of Maize RuBisCO/AroA Gene" Fusion The construct above is cut with NcoI-HindIII releasing the AroA gene. It is then ligated with a 1.5-kbp NcoI-HindIII fragment containing the "transit peptide of the SSU of maize RuBisCO/AroA gene" fusion. The resulting construct exhibits a substitution of the NcoI-HindIII fragments and is a translational fusion "transit peptide of the SSU of sunflower RuBisCO/sequence of 22 amino acids of the SSU of RuBisCO of the mature part of the maize gene/transit peptide of the SSU of maize RuBisCO/AroA gene".

The EcoRI-SalI fragment was ligated with the SalI-SstI fragment containing the 3' nos sequence and the right end of the T-DNA. The resulting EcoRI-SstI fragment comprising "transit peptide of the SSU of sunflower RuBisCO/sequence of 22 amino acids of the SSU of RuBisCO of the mature part of the maize gene/transit peptide of the SSU of maize RuBisCO/AroA gene/3' nos/T-DNA right end" is substituted for the EcoRI-SstI fragment containing the right end of T-DNA of the plasmid 150 A alpha 2 containing the double CaMV promoter. The transcriptional fusion "double CaMV/ transit peptide of the SSU of sunflower RuBisCO/ sequence of 22 amino acids of the SSU of RuBisCO of the mature part of the maize gene/transit peptide of the SSU of maize RuBisCO/AroA gene/3' nos" in the vector 150 A alpha 2 was called pRPA-BL 410. This plasmid is digested with EcoRI and SalI in order to remove the structural gene "optimised transit peptide-mature EPSPS encoding region", pRPA-BL-410 deleted (see FIG. 1).

Example SSUHa: this vector is obtained from the plasmid pRPA-BL-207 (described in European Patent Application 0,337,899) which is digested with EcoRI and HindIII in order to remove the nitrilase-encoding region, pRPA-BL-207 deleted (see FIG. 1).

b. Construction of chimeric genes: pRPA-oxo-03: it is obtained by digesting pRPA-oxo-01 with EcoRI and SalI. The fragment obtained, which encodes the preprotein, is then inserted between the EcoRI and SalI sites downstream of the double CaMV and upstream of the terminator nos respectively. pRPA-oxo-04: it is obtained by digesting pRPA-oxo-02 with EcoRI and SalI. The fragment obtained, which encodes the mature protein, is then inserted between the EcoRI and SalI sites downstream of the double CaMV and upstream of the terminator nos respectively. pRPA-oxo-05: it is obtained by digesting pRPA-oxo-01 with EcoRI and HindIII. The fragment obtained, which encodes the preprotein, is then inserted between the EcoRI and HindIII sites downstream of the double SSUHa and upstream of the terminator nos respectively. pRPA-oxo-06: it is obtained by-digesting pRPA-oxo-02 with EcoRI and HindIII. The fragment obtained, which encodes the mature protein, is then inserted between the EcoRI and HindIII sites downstream of the SSUHa promoter and the terminator nos respectively.

TABLE 1

Schematic representation of the four chimeric genes:

| Identification | Promoter | Oxalate oxidase encoding region | Terminator |
|---|---|---|---|
| pRPA-oxo-03 | dCaMV | preprotein | nos |
| pRPA-oxo-04 | dCaMV | mature | nos |
| pRPA-oxo-05 | SSUHa | preprotein | nos |
| pRPA-oxo-06 | SSUHa | mature | nos |

EXAMPLE 3

Production of Transgenic Colzas:

a. Transformation

Each vector, as described above, is introduced into the nononcogenic *Agrobacterium tumefaciens* strain EHA 101 (Hood et al., (1986) *J. Bacteriol.* 168:1291–1301) carrying the cosmid pTVK 291 (Komari et al. (1086) *J. Bacteriol.* 166:88–94).

The method of transforming colza, Westar variety, is essentially based on that described by Boulter et al. (1990) (*Plant Sci.* 70:91–99), using a bacterial concentration of $2.5 \times 10^9$ per ml (OD 600 nm=1).

b. Regeneration

The method of regeneration is essentially based on that described by Boulter et al. (1990) (*Plant Sci.* 70:91–99). The plants are rooted on the medium of De Block et al. (1989) (*Plant Physiol.* 91:694–701). They are then brought to the flowering stage in a greenhouse.

EXAMPLE 4

Measurement of the Resistance of Colza to *Sclerotinia sclerotiorum*:

In Vitro

Foliar discs: the resistance is measured by weighing the mass of three foliar discs after growing for 11 days on a Murashige and Skoog (MS) medium with hormones, supplemented with 1 mM of oxalic acid.

Under these conditions, it is observed that for the foliar discs obtained from colzas (Westar variety) modified using one of the chimeric genes, pRPA-oxo-03, pRPA-oxo04, pRPA-oxo-05 and pRPA-oxo-06, the mass of the foliar discs increases substantially whereas, in the case of the foliar discs obtained from unmodified colzas, the mass stagnates or even decreases.

Root elongation: the resistance is also measured in vitro by measuring root elongation after growing for two days on water supplemented with 5 mM of oxalic acid. It is observed, in this case, that the roots of colza plants modified with one of the chimeric genes, pRPA-oxo-03, pRPA-oxo-04, are capable of growing and increasing in length, whereas the roots of unmodified colzas show no growth under these conditions.

In Vivo

The resistance in vivo is measured in a greenhouse after contaminating colza plants obtained from the regeneration, as soon as the first flowers appeared, either by depositing *S. sclerotiorum* spores on the petals, the infection of the leaves thereby occurring naturally during defloration, or by directly depositing mycelium or a mycelium-impregnated petal on the leaves. The plants modified by one of the chimeric genes, pRPA-oxo-03, pRPA-oxo-04, pRPA-oxo-05 and pRPA-oxo-06 do not allow the fungus to develop and do not exhibit any symptom of rot characteristic of sclerotiniose, whereas the unmodified plants are rapidly overcome by rot characteristic of the development of *Sclerotinia sclerotiorum*.

What is claimed is:

1. A plant cell transformed with a vector comprising a DNA sequence encoding an oxalate oxidase preprotein comprising an oxalate oxidase signal peptide and an oxalate oxidase mature peptide.

2. The plant cell of claim 1, wherein the plant cell is from a dicotyledon.

3. The plant cell of claim 2, wherein the plant cell is from a Colza.

4. A transformed plant obtained from the cell of claim 1.

5. A plant cell according to claim 1, wherein said vector further comprises a SSUHa promoter.

6. A plant cell according to claim 1 wherein said vector further comprises the double CaMV promoter.

7. A plant cell according to claim 1, wherein said vector comprises the double CaMV promoter followed by that part of the oxalate oxidase cDNA encoding the oxalate oxidase preprotein and the terminator "nos" obtained from the pTi 37 nopaline synthase gene.

8. A plant cell according to claim 1, wherein said vector comprises the SSUHa promoter followed by that part of the oxalate oxidase cDNA encoding the oxalate oxidase preprotein and the terminator "nos" obtained from the pTi 37 nopaline synthase gene.

9. A transformed plant according to claim 4, wherein said plant is a dicotyledon.

10. A transformed plant according to claim 9, wherein said plant is a Colza.

11. A plant according to claim 4, wherein said vector further comprises a SSUHa promoter.

12. A plant according to claim 4, wherein said vector further comprises the double CaMV promoter.

13. A plant according to claim 4, wherein said vector comprises the double CaMV promoter followed by that part of the oxalate oxidase cDNA encoding the oxalate oxidase preprotein and the terminator "nos" obtained from the pTi 37 nopaline synthase gene.

14. A plant according to claim 4, wherein said vector comprises the SSUHa promoter followed by that part of the oxalate oxidase cDNA encoding the oxalate oxidase preprotein and the terminator "nos" obtained from the pTi 37 nopaline synthase gene.

15. The plant cell of claim 1, wherein said DNA sequence encoding an oxalate oxidase preprotein encodes an oxalate oxidase signal peptide and an oxalate oxidase mature peptide comprising the sequence of SEQ ID NO: 1.

16. The plant cell of claim 1, wherein said DNA sequence encoding an oxalate oxidase preprotein has a sequence selected from the group consisting of:

(a) the DNA sequence encoding the oxalate oxidase preprotein pRPA-oxo-01 (SEQ ID NO: 6); and (b) the DNA sequence from nucleotides 86 to 757 of the region encoding the oxalate oxidase preprotein of pRPA-oxo-01 (SEQ ID NO: 6).

17. The plant cell of claim 1 wherein said oxalate oxidase preprotein is the wheat germin preprotein.

18. The plant of claim 4, wherein said DNA sequence encoding an oxalate oxidase preprotein encodes an oxalate oxidase signal peptide and an oxalate oxidase mature peptide comprising the sequence of SEQ ID NO: 1.

19. The plant cell of claim 4, wherein said DNA sequence encoding an oxalate oxidase preprotein has a sequence selected from the group consisting of:

(a) the DNA sequence encoding the oxalate oxidase preprotein pRPA-oxo-01 (SEQ ID NO: 6); and (b) the DNA sequence from nucleotides 86 to 757 of the region encoding the oxalate oxidase preprotein of pRPA-oxo-01 (SEQ ID NO: 6).

20. The plant of claim 4, wherein said oxalate oxidase preprotein is the wheat germin preprotein.

* * * * *

UNITED STATES PATENT AND TRADEMARK OFFICE
CERTIFICATE OF CORRECTION

PATENT NO. : 6,235,530 B1  
DATED : May 22, 2001  
INVENTOR(S) : Georges Freyssinet et al.

Page 1 of 1

It is certified that error appears in the above-identified patent and that said Letters Patent is hereby corrected as shown below:

Column 11,  
Line 23, please delete "TAATTTGTAG" and insert therefor -- TAATTTCTAG --.  
Lines 31-32, please delete           "TTATTGTCGT           967  
CTTTGTTCTT TTCACTGAAC GGAATATATA ATAAGCATTT TCGTA     1012"  
and insert therefor                 -- TTTATTGTCG          967  
TCTTTGTTCT TTTCACTGAA CGGAATATAT AATAAGCATT TTCGTA    1013 --

Signed and Sealed this

Twenty-third Day of April, 2002

Attest:

JAMES E. ROGAN  
Attesting Officer   Director of the United States Patent and Trademark Office

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 24 amino acids
      (B) TYPE: amino acid
      (C) STRANDEDNESS: not relevant
      (D) TOPOLOGY: not relevant (ii) MOLECULE TYPE: peptide (v) FRAGMENT TYPE: N-terminal (ix) FEATURE:
      (A) NAME/KEY: Peptide
      (B) LOCATION: 1
      (D) OTHER INFORMATION: /note= "Amino acid 1 is Xaa wherein
         Xaa = Ile or Ser."

(xi) SEQUENCE DESCRIPTION: SEQ ID NO: 1:

Xaa Asp Pro Asp Pro Leu Gln Asp Phe Xaa Val Ala Asp Leu Asp Gly
1          5                 10              15

Lys Ala Val Ser Val Asn Gly His
        20

(2) INFORMATION FOR SEQ ID NO: 2:

(i) SEQUENCE CHARACTERISTICS:
      (A) LENGTH: 12 amino acids
      (B) TYPE: amino acid
      (C) STRANDEDNESS: not relevant
      (D) TOPOLOGY: not relevant (ii) MOLECULE TYPE: peptide (v) FRAGMENT TYPE: internal (xi) SEQUENCE DESCRIPTION: SEQ ID NO: 2:

His Phe Gln Phe Asn Val Gly Lys Thr Glu Ala Tyr
1          5                 10

(2) INFORMATION FOR SEQ ID NO: 3:

(i) SEQUENCE CHARACTERISTICS:
      (A) LENGTH: 22 base pairs
      (B) TYPE: nucleic acid
      (C) STRANDEDNESS: double
      (D) TOPOLOGY: circular (ii) MOLECULE TYPE: cDNA (xi) SEQUENCE DESCRIPTION: SEQ ID NO: 3:

ATGACCGACC CAGACCCTCT CC                                     22

(2) INFORMATION FOR SEQ ID NO: 4:

(i) SEQUENCE CHARACTERISTICS:
      (A) LENGTH: 7 amino acids
      (B) TYPE: amino acid
      (C) STRANDEDNESS: not relevant
      (D) TOPOLOGY: linear (ii) MOLECULE TYPE: peptide (v) FRAGMENT TYPE: N-terminal (xi) SEQUENCE DESCRIPTION: SEQ ID NO: 4:

Thr Asp Pro Asp Pro Leu Gln
1               5

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: not relevant
        (D) TOPOLOGY: not relevant (ii) MOLECULE TYPE: peptide (v) FRAGMENT TYPE: N-terminal (xi) SEQUENCE DESCRIPTION: SEQ ID NO: 5:

Met Thr Asp Pro Asp Pro Leu Gln
1               5

(2) INFORMATION FOR SEQ ID NO: 6:

(i) SEQUENCE CHARACTERISTICS:
        (A) LENGTH: 1012 base pairs
        (B) TYPE: nucleic acid
        (C) STRANDEDNESS: not relevant
        (D) TOPOLOGY: not relevant (ii) MOLECULE TYPE: cDNA (v) FRAGMENT TYPE: N-terminal (ix) FEATURE:
        (A) NAME/KEY: CDS
        (B) LOCATION: 86..757

(xi) SEQUENCE DESCRIPTION: SEQ ID NO: 6:

```
GCAGCAGCAA CAACCAGTGC CATAGACACT CTCCATCAAC AAACTCTAGC TGATCAATCC         60

TAGCTAAGCT TATTACATAG CAAGC ATG GGG TAC TCC AAA ACC CTA GTA GCT         112
                            Met Gly Tyr Ser Lys Thr Leu Val Ala
                              1               5

GGC CTG TTC GCA ATG CTG TTA CTA GCT CCG GCC GTC TTG GCC ACC GAC         160
Gly Leu Phe Ala Met Leu Leu Leu Ala Pro Ala Val Leu Ala Thr Asp
 10              15                  20                  25

CCA GAC CCT CTC CAG GAC TTC TGT GTC GCC GAC CTC GAC GGC AAG GCG         208
Pro Asp Pro Leu Gln Asp Phe Cys Val Ala Asp Leu Asp Gly Lys Ala
             30                  35                  40

GTC TCG GTG AAC GGG CAC ACG TGC AAG CCC ATG TCG GAG GCC GGC GAC         256
Val Ser Val Asn Gly His Thr Cys Lys Pro Met Ser Glu Ala Gly Asp
         45                  50                  55

GAC TTC CTC TTC TCG TCC AAG TTG GCC AAG GCC GGC AAC ACG TCC ACC         304
Asp Phe Leu Phe Ser Ser Lys Leu Ala Lys Ala Gly Asn Thr Ser Thr
         60                  65                  70

CCG AAC GGC TCC GCC GTG ACG GAG CTC GAC GTG GCC GAG TGG CCC GGT         352
Pro Asn Gly Ser Ala Val Thr Glu Leu Asp Val Ala Glu Trp Pro Gly
     75                  80                  85

ACC AAC ACG CTG GGT GTG TCC ATG AAC CGC GTG GAC TTT GCT CCC GGA         400
Thr Asn Thr Leu Gly Val Ser Met Asn Arg Val Asp Phe Ala Pro Gly
 90              95                  100                 105

GGC ACC AAC CCA CCA CAC ATC CAC CCG CGT GCC ACC GAG ATC GGC ATC         448
Gly Thr Asn Pro Pro His Ile His Pro Arg Ala Thr Glu Ile Gly Ile
             110                 115                 120

GTG ATG AAA GGT GAG CTT CTC GTG GGA ATC CTT GGC AGC CTC GAC TCC         496
Val Met Lys Gly Glu Leu Leu Val Gly Ile Leu Gly Ser Leu Asp Ser
```

-continued

```
             125                 130                 135
GGG AAC AAG CTC TAC TCG AGG GTG GTG CGC GCC GGA GAG ACG TTC CTC    544
Gly Asn Lys Leu Tyr Ser Arg Val Val Arg Ala Gly Glu Thr Phe Leu
        140                 145                 150

ATC CCA CGG GGC CTC ATG CAC TTC CAG TTC AAC GTC GGT AAG ACC GAG    592
Ile Pro Arg Gly Leu Met His Phe Gln Phe Asn Val Gly Lys Thr Glu
155                 160                 165

GCC TCC ATG GTC GTC TCC TTC AAC AGC CAG AAC CCC GGC ATT GTC TTC    640
Ala Ser Met Val Val Ser Phe Asn Ser Gln Asn Pro Gly Ile Val Phe
170                 175                 180                 185

GTG CCC CTC ACG CTC TTC GGC TCC AAC CCG CCC ATC CCA ACG CGC GTG    688
Val Pro Leu Thr Leu Phe Gly Ser Asn Pro Pro Ile Pro Thr Arg Val
            190                 195                 200

CTC ACC AAG GCA CTC CGG GTG GAG GCC AGG GTC GTG GAA CTT CTC AAG    736
Leu Thr Lys Ala Leu Arg Val Glu Ala Arg Val Val Glu Leu Leu Lys
                205                 210                 215

TCC AAG TTT GCC GCT GGG TTT TAATTTGTAG GAGCCTTCCC TGAAATGATA       787
Ser Lys Phe Ala Ala Gly Phe
            220

ATTATATAAT TCCATATATG CATGCTAGCA AAATTTAATA ATTCTCACCA GAAGACATGT  847

ATTCAAGTTT CAGGTTAATC TCGCATGTAG TCGTGTAATA AGATTGAACA AGTTAGCCTC  907

ATGGTGTAGC CTTCGATCAG AACCAATATG AGGAATTGAA TGTACTACTT TTATTGTCGT  967

CTTTGTTCTT TTCACTGAAC GGAATATATA ATAAGCATTT TCGTA                  1012

(2) INFORMATION FOR SEQ ID NO: 7:

(i) SEQUENCE CHARACTERISTICS:
        (A) LENGTH: 224 amino acids
        (B) TYPE: amino acid
        (D) TOPOLOGY: linear (ii) MOLECULE TYPE: protein (xi) SEQUENCE DESCRIPTION: SEQ ID NO: 7:

Met Gly Tyr Ser Lys Thr Leu Val Ala Gly Leu Phe Ala Met Leu Leu
 1               5                  10                  15

Leu Ala Pro Ala Val Leu Ala Thr Asp Pro Asp Pro Leu Gln Asp Phe
                20                  25                  30

Cys Val Ala Asp Leu Asp Gly Lys Ala Val Ser Val Asn Gly His Thr
            35                  40                  45

Cys Lys Pro Met Ser Glu Ala Gly Asp Asp Phe Leu Phe Ser Ser Lys
        50                  55                  60

Leu Ala Lys Ala Gly Asn Thr Ser Thr Pro Asn Gly Ser Ala Val Thr
65                  70                  75                  80

Glu Leu Asp Val Ala Glu Trp Pro Gly Thr Asn Thr Leu Gly Val Ser
                85                  90                  95

Met Asn Arg Val Asp Phe Ala Pro Gly Thr Asn Pro Pro His Ile
            100                 105                 110

His Pro Arg Ala Thr Glu Ile Gly Ile Val Met Lys Gly Glu Leu Leu
        115                 120                 125

Val Gly Ile Leu Gly Ser Leu Asp Ser Gly Asn Lys Leu Tyr Ser Arg
    130                 135                 140

Val Val Arg Ala Gly Glu Thr Phe Leu Ile Pro Arg Gly Leu Met His
145                 150                 155                 160

Phe Gln Phe Asn Val Gly Lys Thr Glu Ala Ser Met Val Val Ser Phe
                165                 170                 175
```

-continued

```
Asn Ser Gln Asn Pro Gly Ile Val Phe Val Pro Leu Thr Leu Phe Gly
            180             185             190

Ser Asn Pro Pro Ile Pro Thr Arg Val Leu Thr Lys Ala Leu Arg Val
            195             200             205

Glu Ala Arg Val Val Glu Leu Leu Lys Ser Lys Phe Ala Ala Gly Phe
            210             215             220
```